United States Patent [19]
Sjoestrand

[11] Patent Number: 5,575,283
[45] Date of Patent: Nov. 19, 1996

[54] DEVICE FOR DETERMINING AN OPENING PRESSURE IN THE LUNGS

[75] Inventor: Ulf Sjoestrand, Uppsala, Sweden

[73] Assignee: Siemens-Elema AB, Solna, Sweden

[21] Appl. No.: 387,186

[22] Filed: Feb. 13, 1995

[30] Foreign Application Priority Data

Feb. 14, 1994 [SE] Sweden ................................. 9400487

[51] Int. Cl.$^6$ ................................................. A61M 16/00
[52] U.S. Cl. ................................ 128/204.23; 128/204.18
[58] Field of Search ........................ 128/204.18, 204.21, 128/204.22, 204.23, 204.26, 205.24

[56] References Cited

U.S. PATENT DOCUMENTS

| | | | |
|---|---|---|---|
| 4,036,221 | 7/1977 | Hillsman et al. | 128/204.23 |
| 4,323,064 | 4/1982 | Hoenig et al. | 128/204.21 |
| 4,587,967 | 5/1986 | Chu et al. | 128/205.11 |
| 4,957,107 | 9/1990 | Sipin | 128/204.27 |
| 5,400,777 | 3/1995 | Olsson et al. | |

FOREIGN PATENT DOCUMENTS 2121292 12/1983 United Kingdom .

OTHER PUBLICATIONS

"Open Up the Lung and Keep the Lung Open," Lachmann, Intensive Care Med., vol. 18, (1992), pp. 319–321.
"Mechanical Ventilation, Slutsky, ACCP Concensus Conference," Chest vol. 104 (1993), pp. 1833–1859.

Primary Examiner—V. Millin
Assistant Examiner—William J. Deane, Jr.
Attorney, Agent, or Firm—Hill, Steadman & Simpson

[57] ABSTRACT

Most alveoli could collapse in different illnesses and injuries to a lung. A relatively high positive pressure, which could in itself damage the lung or impede its healing, is required to open the alveoli. A positive pressure is often applied at the end of the expiratory phase in order to keep the alveoli open throughout entire respiratory cycles. A ventilator is disclosed wherein an opening pressure for the lung can be determined from measurement values for the pressure and the volume of air supplied to the lung. The ventilator registers the measurement values and determines the opening pressure from the relationship between measurement values for pressure and for volume. The determined opening pressure can then be used by a physician for setting an appropriate end expiratory pressure (PEEP) for the respiratory phase or be used by a control unit in the ventilator for automatic setting of an appropriate end expiratory pressure.

22 Claims, 4 Drawing Sheets

DEVICE FOR DETERMINING AN OPENING PRESSURE IN THE LUNGS

BACKGROUND OF THE INVENTION

1. Field of the Invention

The present invention relates to a ventilator/respirator for regulating the flow of air to, and the pressure of air in, the lungs, having a pressure gauge for determining the pressure of air in the lung and a volume-determining device for determining the volume of air supplied to the lung.

2. Description of the Prior Art

In a healthy lung, air passes during inspiration (inhalation) through airways and bronchi to the alveoli in the lung. An exchange of gas occurs in the alveoli, whereby blood is oxygenated while carbon dioxide is simultaneously transferred to air in the alveoli. During expiration (exhalation), air enriched with carbon dioxide is extracted from the lung, permitting the entry of fresh air. Since a healthy lung has large compliance, i.e., flexibility, a relatively large volume of air can be inhaled every time a person takes a breath without excessive increases in the pressure of air in the lung. Efficient exchange of oxygen and carbon dioxide is essential to the load on the heart and to the supply of vital oxygen to the body. When gas exchange becomes impaired, the load on the heart increases because the heart has to pump more blood through the lungs.

As a result of injuries or disease, the function of the lung can be affected to such a degree that a life-threatening condition could develop. For example, the alveoli might collapse, impairing or, at worst, preventing the essential exchange of gas between air in the alveoli and blood in the lungs capillaries. Another possibility is that the compliance of the lung could decline so much that an insufficient volume of air is inhaled in each breath. Connecting the damaged lung to a ventilator/respirator may then be necessary to keep the patient alive. A ventilator/respirator can subject the lung to an air pressure large enough to open the alveoli so sufficient gas exchange can take place. The operation of such a device for opening the lung and maintaining it open is described in an article entitled "Open up the lung and keep the lung open" by B. Lachmann, Intensive Care Medicine (1992) 18:319–321. Air at a relatively high pressure must be supplied to the lung in order to open the alveoli, whereas a much lower pressure is needed during ventilator/respirator breathing to keep the alveoli open once they have been opened. At the same time, the risk of lung trauma in forced respiration increases at higher pressures (barotrauma) and/or large volumes of breathing gas (volutrauma), especially if lung compliance is simultaneously poor.

Another consideration in this context is that a patient on a ventilator/respirator must be weaned off the unit for a certain period of time before normal, spontaneous breathing resumes. The requisite weaning time can be considerably shortened if the forced respiration is performed in such a way that it does not impose needlessly heavy loads on the lung with high absolute pressures, large changes in pressure and/or large volumes of air/breath. Non-traumatic treatment of a lung also promotes healing, which is obviously advantageous to the patient. Faster healing also conveys major economic benefits, especially in intensive care etc. where beds are very expensive.

Modern ventilators/respirators operate according to various ventilation principles which strive to keep a lung completely open by creating some form of positive pressure in the lung. This can be accomplished, e.g., by having the ventilator generate a positive end expiratory pressure (PEEP) or by reducing the relative duration of expiration in order to create a positive pressure in the lung at the end of expiration (intrinsic PEEP), both methods keeping the alveoli open. A third option is to increase the breathing rate, thereby retaining a surplus of air in the lung and creating a positive pressure which keeps the alveoli open. The latter method greatly depends on the ratio between the duration of inspiration and expiration.

Another factor to be taken into account, making it harder for the physician to select a treatment method for a patient, is the circumstance that all lungs are individual and respond to treatment in different ways, thereby affecting the pressure at which the lungs are opened and the pressure required to keep the lungs open. In addition, every individual lung's responses to its prevailing condition varies. Adapting treatment accordingly is especially important when a sick or damaged lung is healing.

SUMMARY OF THE INVENTION

An object of the present invention is to provide a ventilator/respirator of the type having a pressure gauge for determining the pressure in a lung and a volume-determining device for determining the volume of air supplied to the lungs, which solves the above-mentioned problems and which makes it easier for medical staff to use a ventilation mode best suited to each patient's needs.

This object is achieved in a ventilator/respirator constructed in accordance with the principles of the present invention having a registration unit, connected to the pressure gauge and a volume-determining device, for registering the determined air pressure and the determined air volume during at least part of an inspiratory phase, and a calculation unit, connected to the registration unit in order to determine, from the relationship between registered pressure measurement values and volume measurement values, an opening pressure in the lung at which opening pressure several of the alveoli in the lung are inflated.

In a lung in which the alveoli have collapsed, only the pressure in the lung increases, in principle, at the start of a forced inspiration. In this situation the volume supplied to the lung is marginal. The volume increases as the alveoli open, and the relationship between pressure and volume increasingly begins to resemble the relationship prevailing in a healthy lung. When the lung has filled, no additional air can be supplied. Pressure does not increase unless inspiration is allowed to continue. An opening pressure can be set on the basis of the registered values. In principle, this opening pressure can be defined as a pressure at which most collapsed alveoli have been inflated or are open. With knowledge of this opening pressure, the physician can tailor the form of treatment, especially the lowest pressure to be imposed on the lung, to the individual patient. The actual treatment of the lungs can be based on the supply of a specific volume of air in each breath. This volume of air is often far less than the maximum volume the lungs can hold.

It is an advantage if the ventilator/respirator comprises a display unit, preferably a digital display or a monitor, connected to the calculation unit to display the opening pressure. This gives the physician direct access to the specific opening pressure and enable him or her to adapt respirator treatment accordingly.

In an embodiment of the ventilator/respirator of the invention, a control unit is connected to the calculation unit and to an expiratory valve for automatic regulation of the expiratory valve depending on the opening pressure determined by the calculation unit so that a positive end expiratory pressure (PEEP), greater than ambient pressure, is maintained in the lung at the end of each expiratory phase.

This achieves automatically regulated control of a ventilator/respirator, ensuring that the patient receives a positive end pressure which is low enough to prevent needless trauma to the lung but which is still high enough to ensure optimum lung function.

In this context it is an advantage if the control unit sets the lowest end pressure in the lung at a specific percent of the opening pressure, preferably 50–100% of the opening pressure.

In another embodiment of the ventilator/respirator of the invention, the ventilator/respirator supplies a predetermined volume of air to the lung during the inspiratory phase of every respiratory cycle, the registration unit registers pressure in the lung at the end of the inspiratory phase of every respiratory cycle, and the calculation unit determines the relative increase in pressure which occurs in the lung when the predetermined volume of air is supplied to the lung and also determines, over a specific number of respiratory cycles, whether the relative pressure increase is declining, increasing or unchanged.

Once the alveoli have opened, the patient is usually ventilated with relatively small volumes, compared to the maximum volumes a lung is able to hold. Pressure, even at these small volumes, is nonetheless affected by the state of the lung. As a lung heals, for example, the increase in the pressure of the supplied volume of gas declines at every breath. This means that a new determination of the opening pressure could be performed for determination of a new PEEP, adapted to the new state of the lung. Since the pressure at the end of the inspiratory phase depends on the volume of air supplied and the state of the lung, a completely new evaluation of the opening pressure is not necessary for determining a new PEEP. Instead, the ventilator/respirator can automatically reduce PEEP until the pressure increase caused by the volume of supplied air at the beginning of treatment with the specific PEEP value is again present. In other words, the ventilator/respirator continuously strives to maintain a specific relative pressure-volume curve for each breath by changing the absolute pressure (i.e. PEEP). The relative pressure-volume curve is thus displaced along the pressure axis in a pressure-volume diagram.

Alternatively, or as a complement, the ventilator/respirator can be devised so that the calculation unit determines the opening pressure at specific intervals. This opening pressure will vary, depending on the health of the lung, as noted above. Pressure is accordingly always kept as low as possible so as to prevent trauma to the lung.

The ventilator/respirator can appropriately be devised so the display unit displays a suitable PEEP based on the opening pressure, whereby the physician can decide if the proposed end pressure is to be set. The display unit can also be used for indicating that a new determination of the opening pressure is warranted or that a new PEEP may be warranted.

Since the determined opening pressure designates, in principle, the pressure at which the lung opens or has just opened, it can be utilized as the desired end pressure when other ventilation principles are employed, whereupon the control unit can regulate or propose, via the display unit, the duration of expiration, the ratio between inspiration and expiration etc.

There are numerous of ways to determine opening pressure from the relationship between measured pressure values and measured volume values. One way achieved in accordance with the invention is that the calculation unit sets the opening pressure at the pressure at which the registered volume of supplied air exceeds a specific threshold value.

As noted above, the pressure in a lung with collapsed alveoli increases, without any major increase in the volume of air supplied to the lung, until the alveoli begin inflating and opening up. In this situation, the volume of supplied air will start increasing more sharply in relation to the pressure during the inspiratory phase. When an appropriate threshold value for the supplied volume of air is set, opening pressure can be set at a pressure at which at least several of the alveoli have opened.

Another way of determining opening pressure is achieved in accordance with the invention by the calculation unit setting the opening pressure at the pressure at which a specific increase in pressure causes an increase in volume which exceeds a specific volume value.

For the same reason as stated above, the increase in volume when the alveoli start opening will be greater than previously, viewed over a specific pressure interval. When the pressure is determined at which a small increase in pressure produces an adequate increase in volume, the opening pressure can be set at this pressure.

A third way of determining the opening pressure is achieved in accordance with the invention by the calculation unit establishing a curve which is optimally fitted to the values registered for pressure and volume within a specific interval of the inspiratory phase, preferably between a minimum volume value and a maximum volume value, and setting the opening pressure at the pressure at which the fitted curve intersects a specific volume value, preferably a zero value.

Once a damaged lung has opened, it behaves more like a healthy lung, even if impaired compliance may require a greater increase in pressure for the supply of a given volume of air to the lung. Thus a curve can be fitted, within an interval of registered pressure values and volume values, which, in principle, follows the registered values in the interval and which can ultimately be used for determining the pressure at which the lung begins to open. Using an intersection point with a volume value for determining the opening pressure is most appropriate. An appropriate value for volume is zero. It should again be noted that the volume value refers to the volume supplied to the lung and not the volume of air in the lung, which always retains a residual volume of air. It was stated above that the interval within which the curve is to be maximally fitted to the registered values should preferably be defined by a minimum volume and a maximum volume. The interval can naturally be defined by a minimum pressure and a peak pressure or any combination thereof. The interval limits can either be set by a physician, or by the control unit on the basis of programmed conditions. In the latter instance, changes in volume for minor changes in pressure could be used, for example, i.e., the interval can be set at the interval within which the increase in volume in relation to the increase in pressure is greater than a defined limit value.

One advantageous method for fitting a curve to the registered value is the least squares method.

The calculation unit can be devised to fit either a linear curve or a non-linear curve or a Gaussian distribution.

DESCRIPTION OF THE PREFERRED EMBODIMENTS

Figure 1:
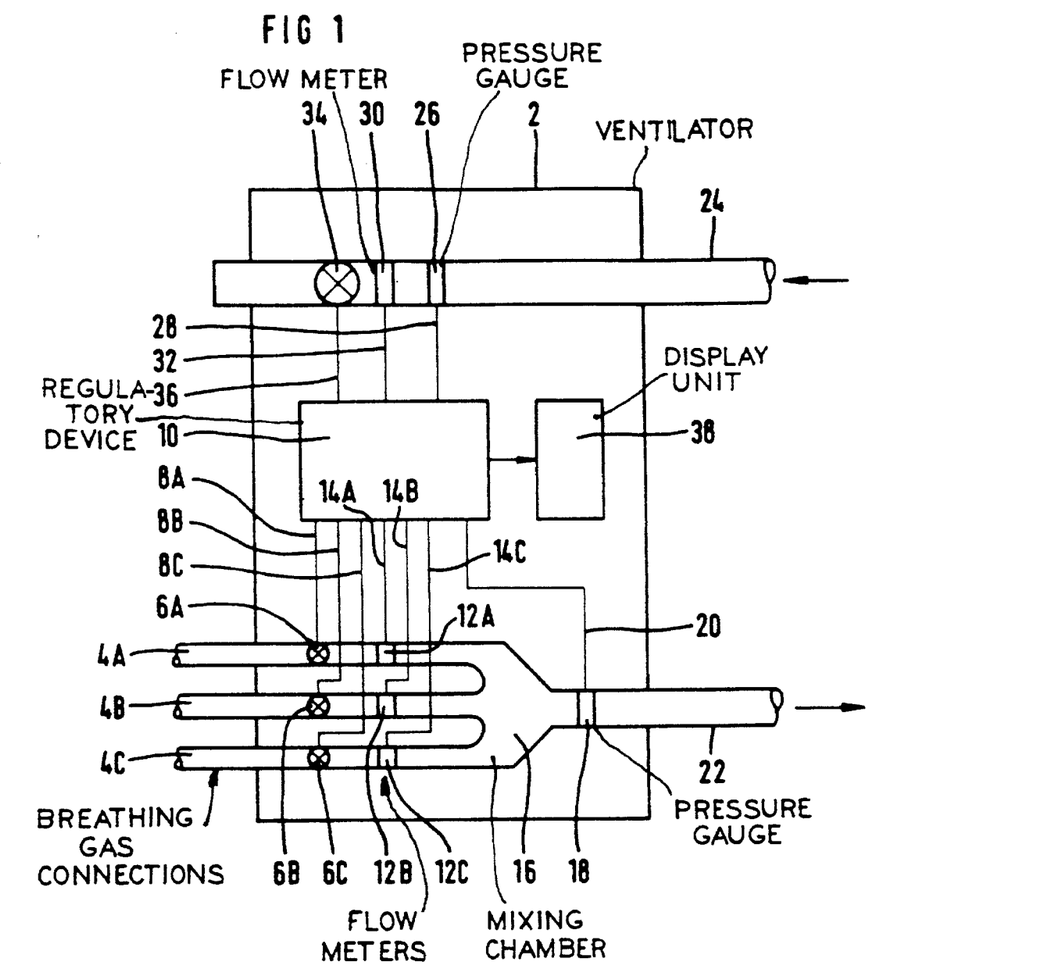
FIG. 1 is a schematic illustration of one embodiment of a ventilator/respirator constructed in accordance with the principles of the present invention.

The ventilator 2 in FIG. 1 has three gas connections 4A, 4B and 4C through which breathing gases can be supplied to the ventilator 2. Each gas connection 4A, 4B and 4C is equipped with an inspiratory valve 6A, 6B and 6C to regulate the flow of the respective gas. One or more of the gas connections 4A, 4B and 4C can be active in supplying the breathing gases which could be, e.g., air and oxygen. The inspiratory valves 6A, 6B, 6C are controlled by a regulatory device 10 via control lines 8A, 8B and 8C. Three flow meters 12A, 12B and 12C are connected to the respective gas connection 4A, 4B and 4C so that flow through the respective gas connection 4A, 4B and 4C is controlled as accurately as possible. The values determined for the respective gas flow are sent to the regulatory device 10 via measurement signal lines 14A, 14B and 14C. The components of the breathing gases which are used are mixed in a mixing chamber 16 before being delivered. The gas passes from the ventilator 2, via an inspiratory tube 22, to a patient's lungs during inspiration. A first pressure gauge 18 measures the pressure of air on the inspiratory side and sends this information to the regulatory device 10 via a first pressure signal line 20.

During expiration, expired gas from the patient's lungs is sent back to the ventilator 2, via an expiratory tube 24, in which pressure on the expiratory side is measured in a second pressure gauge 26, and the information is sent to the regulatory device 10 via a second pressure signal line 28. Expiratory flow on the expiratory side is also measured in a fourth flow meter 30, and this measurement signal is sent to the regulatory device 10 via a measurement signal line 32. The ventilator 2 is equipped with an expiratory valve 34, which is controlled by the regulatory device 10 via a control line 36, in order to control expiration and create a positive pressure in the lung at the end of expiration, i.e., a PEEP. The regulatory device 10 controls the patient's inspiration and expiration on the basis of an operating mode selected by a physician. With a display unit 38, information, such as values set and measured actual values, is shown on one or a number of displays and bar graphs or on a monitor. As will be described below, the display unit 38 can also be used for displaying a recommended PEEP. Depending on the operating mode, this PEEP, or a modified PEEP based on the recommended PEEP, can be automatically implemented or may be implemented by entry of instructions by a physician to the regulatory device 10 via a suitable control panel 49 (shown in FIG. 2).

The inspiratory tube 22 and the expiratory tube 24 are connectable to the airways, and thus to the lungs of a patient.

Figure 2:
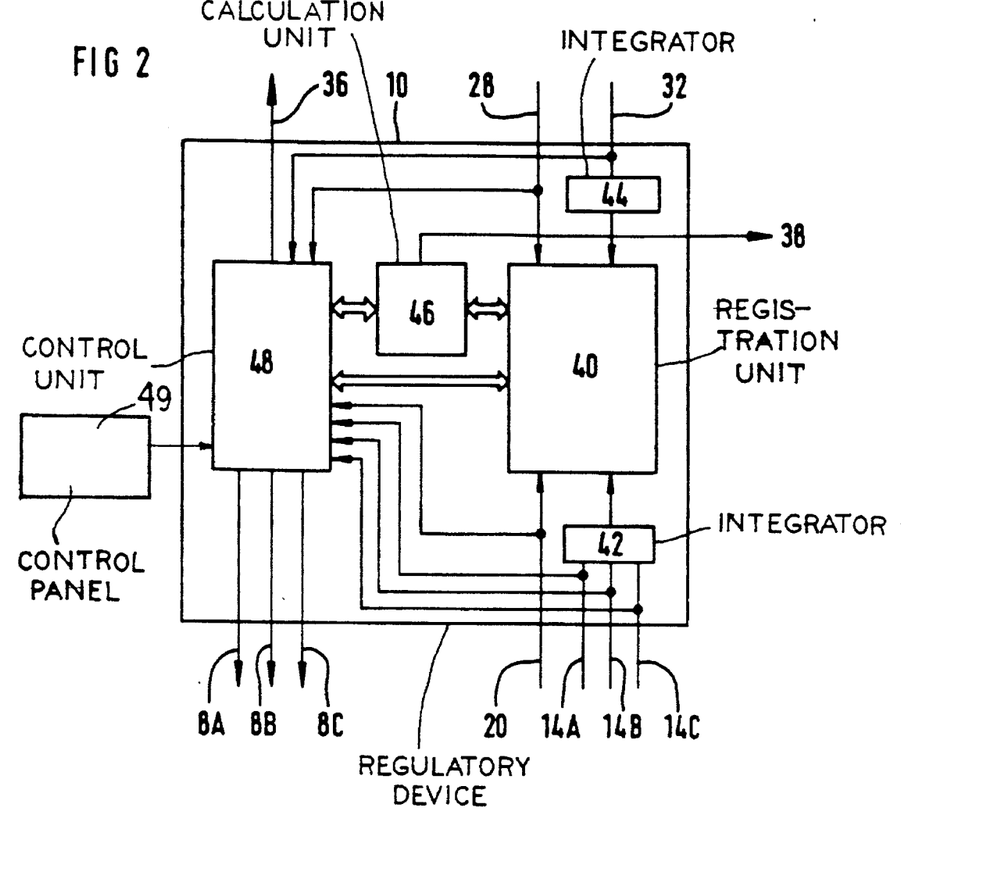
FIG. 2 is a block diagram of part of the control and regulatory system of the ventilator/respirator of FIG. 1.

FIG. 2 is a block diagram showing the regulatory device 10. Pressures measured in the inspiratory section and the expiratory section of the ventilator 2 are registered in a registration unit 40. Flow measurement values from the inspiratory section are sent to a first integrator 42, via the signal lines 14A, 14B and 14C, in which the volume of the gas supplied to the patient at every inhalation is calculated. Integration is performed continuously from the beginning of inspiration, making it possible to determine at any given moment the total volume supplied and the changes in volume up to that given moment. In the corresponding manner, the flow measurement value is integrated on the expiratory side in a second integrator 44, and the value for the supplied volume of air is sent to the registration unit 40. An opening pressure at which most alveoli in the lungs are opened can be determined in a calculation unit 46 from the values registered for pressure and volume. The manner of and reason for determining opening pressure are described below in conjunction with the descriptions of FIGS. 3-5. All measurement values are also sent to a control unit 48 in the regulatory device 10. The control unit 48 controls all functions in the ventilator 2. As FIG. 2 shows, the control unit 48 especially controls the inspiratory valves 6A, 6B and 6C via the control lines 8A, 8B and 8C and the expiratory valve 34 via the control line 36. The registration device 40, the calculation unit 46 and the control unit 48 can communicate with each other, as designated in FIG. 2 with data busses. A signal line runs from the calculation unit 46 to the display unit 38 to indicate the opening pressure set. Other set or calculated parameters could also be shown on the display unit 38.

Figure 3:
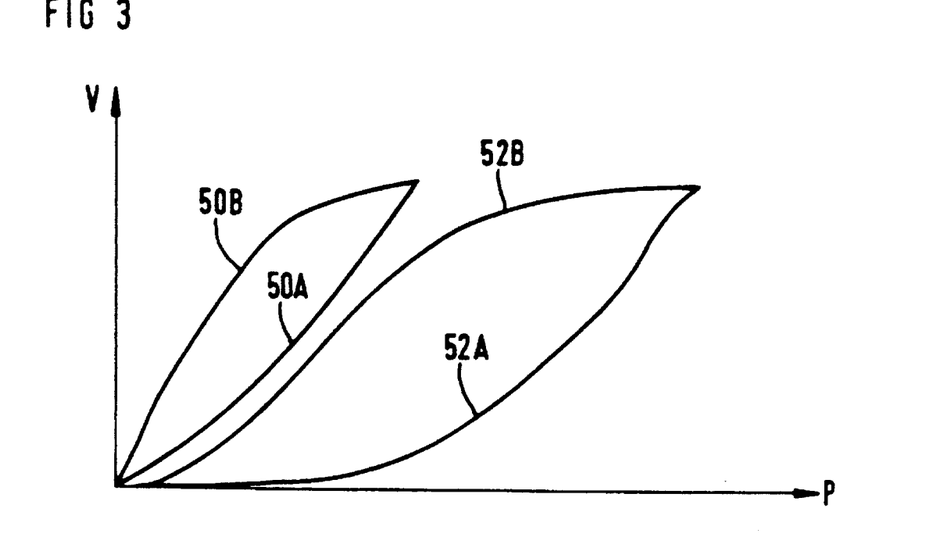
FIG. 3 is a pressure-volume diagram illustrating the difference between a healthy lung and sick lung.

FIG. 3 shows a first respiratory curve 50 for a healthy lung and a second respiratory curve 52 for a damaged or sick lung in which a number of alveoli have collapsed. In the healthy lung, pressure and the supplied volume change during inspiration according to curve 50A. Curve 50B shows pressure and the volume measured during expiration. The differences compared to the sick lung are very apparent. During inspiration, pressure in the sick lung, curve 52A, rises without any corresponding increase in the volume supplied. This is because a certain pressure is required to start opening the alveoli. The required pressure is by no means constant but varies from patient to patient and in each patient. Factors affecting opening pressure are, e.g., the percent of collapsed alveoli, the size of the collapsed alveoli and the lung's compliance. When the required opening pressure has been reached, the inspiratory curve 52A will basically resemble the curve for a healthy lung, whereas the expiratory curve 52B is more drawn out than for a healthy lung. Even when the alveoli have opened, the lung's compliance will have an impact on the inspiratory curve 52A. Poor compliance results in a flatter curve with a larger increase in pressure in relation to the increase in volume than is the case with a lung with greater compliance.

If the alveoli are allowed to collapse after each expiration, it would be necessary to open them at every inspiration. This could subject the lung to a needlessly high end pressure at each inspiration and large variations in pressure during each respiratory cycle. Moreover, excessive volumes of air could be supplied to the lung. All these factors are capable of damaging the lung and prolonging its recovery. In addition, weaning the patient off the ventilator would be more difficult.

Thus keeping the alveoli open is necessary while peak pressure and variations in pressure in the lungs are simultaneously kept to a minimum when a specific volume of air is supplied to the lungs.

Figure 4:
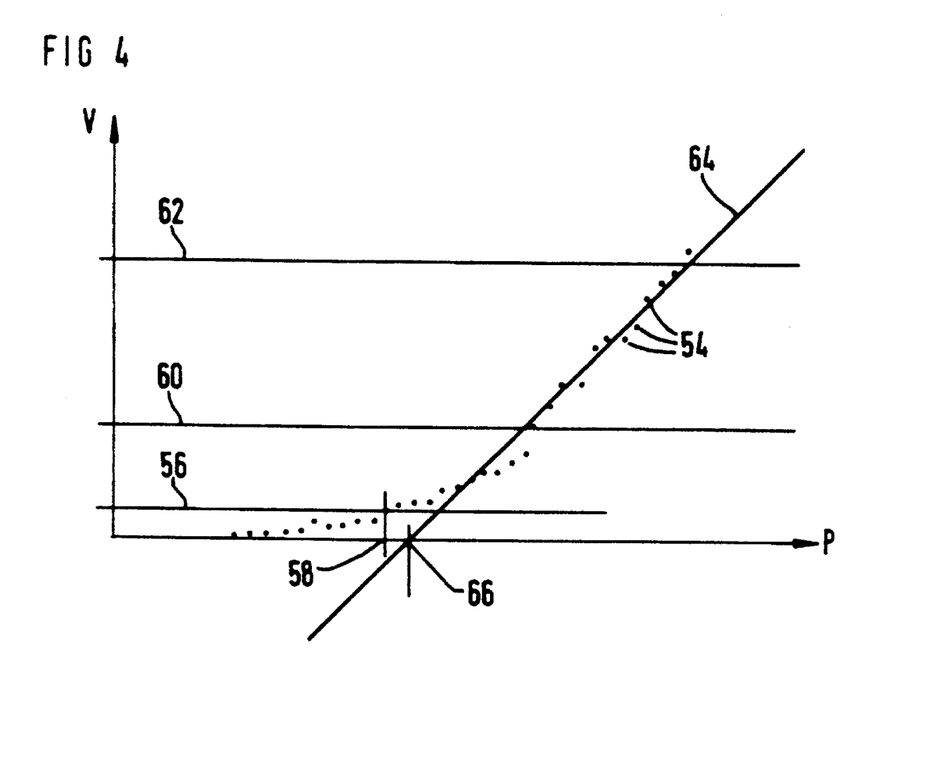
FIG. 4 illustrates two ways with which an opening pressure can be determined according to the invention.

FIG. 4 shows two ways of obtaining an opening pressure at which at least several of the alveoli have opened. In this context, the term "opening pressure" does not refer to the pressure required to ensure that all the alveoli have opened. "Opening pressure", as applied in conjunction with the invention, is instead the pressure which, when determined according to the invention, makes possible nontraumatic treatment of a sick or damaged lung and which facilitates the healing process or reduces weaning time. On the basis of this opening pressure, the physician can, e.g., set an appropriate end pressure, PEEP, during the expiratory phase. This end pressure keeps the alveoli open until the start of the next inspiration.

A number of measurement points 54 have been marked in the pressure-volume diagram to illustrate the two described modes. The marked measurement points 54 do not represent all the possible measurement points but have been selected as a number making it possible to clearly illustrate the two modes. The registration of measurement values by the registration unit 40 can be performed by, e.g., sampling at a relatively fast sampling rate, thereby supplying a number of measurement points greater than the number of marked points and naturally improving the possibility of finding the most relevant opening pressure. At least 200 measurement points are suitable for obtaining a good curve fit.

The first mode is based on the fact that only a small volume of air can be supplied to the lungs before the alveoli have opened. A threshold value 56 has therefore been entered in the pressure-volume diagram. When the measurement values for the supplied volume reaches this threshold value, the corresponding pressure is defined as the opening pressure 58.

The second mode arrives at the opening pressure by fitting a curve to at least some of the measurement values. A minimum volume of 60 and a peak volume of 62 have been marked in the pressure-volume diagram in FIG. 4, and only measurement values between these two volume limits are employed in fitting a curve 64. In this instance, the curve 64 was determined by the least squares method for the established interval. Here, the intersection of the fitted curve 64 with the zero line of the volume axis designates the opening pressure 66.

Figure 5:
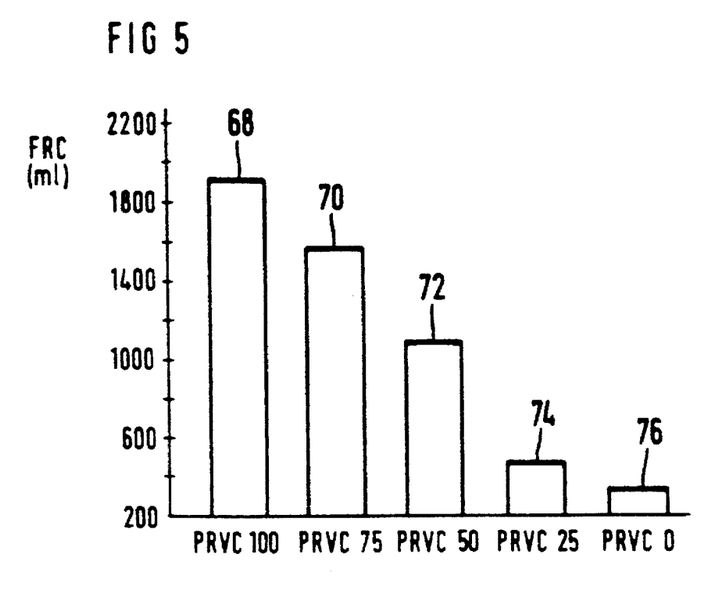
FIG. 5 illustrates the difference between various end pressures in relation to the functional residual capacity of a lung.

The determined opening pressure 58 or 66 can then be used for establishing a PEEP pressure. FIG. 5 shows how the choice of PEEP affects the functional residual capacity (FRC) of a lung with a given ventilator operating mode. The first column, 68 is obtained when PEEP pressure is set at 100% of the determined opening pressure. The second column 70 shows the functional residual capacity obtained when PEEP is set at 75% of the determined opening pressure. The third column 72 shows FRC for a PEEP which is 50% of the determined opening pressure. The fourth column 74 shows FRC for a PEEP which is 25% and the fifth column shows FRC at 0%. Similar differences at different PEEPs can also be shown for the partial pressure of carbon dioxide ($CO_2$) and oxygen ($O_2$) in blood from the lungs (arterial blood) and other pulmonary parameters.

Figure 6:
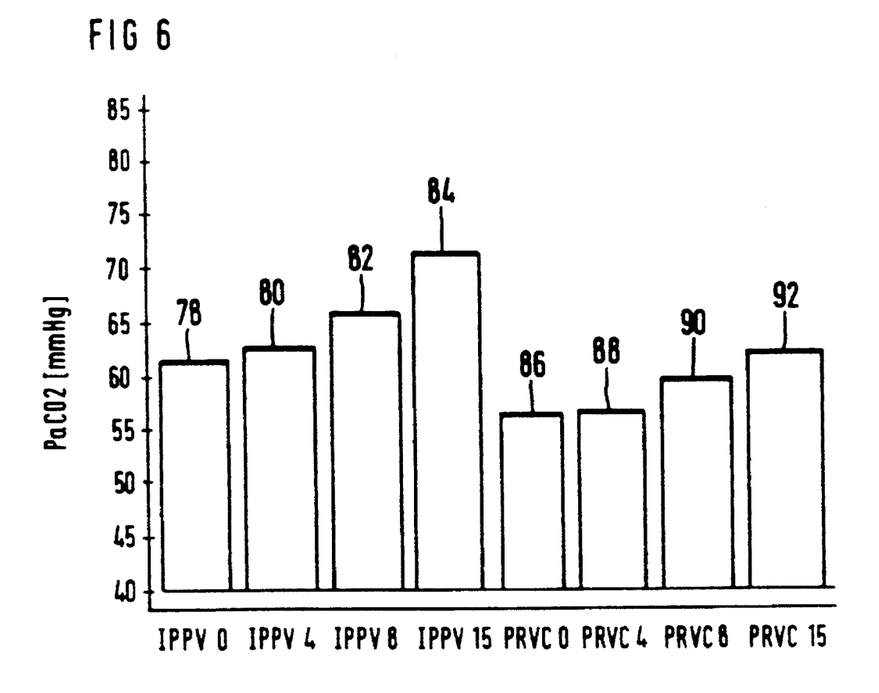
FIG. 6 illustrates variations in the partial pressure of $CO_2$ in the blood at different PEEP's for two ventilation principles.

FIG. 6 illustrates differences in the partial pressure of $CO_2$ at different end expiratory pressures for two different ventilation modes. The four columns 78, 80, 82 and 84 to the left in FIG. 6 show the results in an operating mode referred to as intermittent positive pressure ventilation (IPPV) for the end expiratory pressures 0, 4, 8 and 15 centimeter columns of water, cm $H_2O$ (positive pressure in relation to atmospheric pressure). The four columns 86, 88, 90 and 92 to the right show the results at the same end pressure for an operating mode referred to as pressure-regulated volume control (PRVC). Measurements here were made on healthy lungs. This means that the opening pressure, calculated according to the curve fitting method above, was around 4 cm $H_2O$, i.e., the columns 80 and 88. The effect of an excessive PEEP is apparent for both ventilation modes. The same results have been shown for sick/damaged lungs.

Keeping the lungs open also contributes to reducing the load on the patient's heart. A lung which works more effectively improves the exchange of gas between blood and air in the alveoli. The volume of blood flowing through the lungs does not then have to be as large as in the case of a less effective lung. A reduced need for perfusion of the lung naturally reduces the load on the heart which, accordingly, does not need to pump as much blood. This is particularly important for patients in intensive care, etc. Another consequence of more effective gas exchange is that the composition of air supplied to the patient can be changed. In particular, the oxygen content can be reduced.

Other procedures can be used for determining opening pressure. For example, a non-linear curve can be fitted to measurement values within the selected interval. In addition, a curve can be fitted to all the measurement values in an inspiratory cycle, and the opening pressure can be determined from the derivative of the established curve. In addition, the limitation of a minimum volume and a maximum volume in curve fitting can vary. The interval can be set in the form of a minimum pressure and a peak pressure or as a combination thereof. Another possible combination of different modes for determining the opening pressure is to first fit a curve to all measurement values, delineate an area in which the derivative maintains certain values, and fit a new curve within this area. The new curve can then be used as described above in conjunction with the description of FIG. 4.

The ventilator 2 can even automatically set an appropriate PEEP and determine the opening pressure at regular intervals in the manner described above in order to adapt pressure to the lung.

Figure 7:
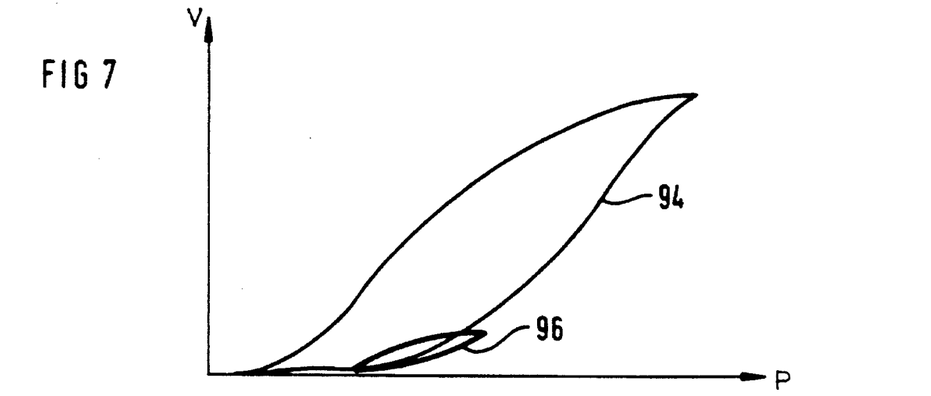
FIG. 7 shows a treatment curve and an evaluation curve for determining opening pressure in accordance with the invention.

The lung is normally ventilated with a volume of air which is less than maximum lung capacity. This is shown in FIG. 7 in which an evaluation curve 94 for determining the opening pressure and a treatment curve for a patient are entered in a pressure-volume diagram. Since the ventilator 2 registers pressure and measures the volume of air, automatic self-regulation of PEEP can be programmed without the need to repeat determination of the opening pressure. This can be accomplished when the ventilator 2 calculates, after a physician has determined the volume of air the patient is to receive in each breath, e.g., 0.5 liter, the pressure increase caused by the selected volume of air and then strives to keep this pressure increase constant. In principle, the increase in pressure during inspiration will only depend on the condition of the lung. As the lung heals, the treatment curve 96 will be compressed along the pressure axis. When the end expiratory pressure is reduced, the treatment curve 96 resumes its original morphology. Its position on the pressure axis thus will, in principle, be shifted. It is therefore advantageous if the ventilator is allowed to automatically reduce the PEEP value so the treatment curve 96 can retain its morphology.

The opening pressure which is established can also be utilized for determining other appropriate control parameters, such as expiratory duration, when an intrinsic PEEP is to be avoided or maintained or for determining the ratio between inspiration and expiration in order to achieve the corresponding PEEP at the end of expiration. The most salient point is that a ventilator/respirator according to the invention provides a parameter which increases the physician's ability to provide a patient with the best possible respiratory care.

Although modifications and changes may be suggested by those skilled in the art, it is the intention of the inventors to embody within the patent warranted hereon all changes and modifications as reasonably and properly come within the scope of their contribution to the art.

I claim as my invention:

1. A ventilator comprising:

respiratory-assist means, connectable to a patient, for assisting respiration of said patient by supplying a regulated flow of air to the lungs of said patient, said regulated flow of air having a volume and producing air pressure in the lungs;

pressure gauge means for measuring said air pressure in the lungs;

volume-determining means for measuring the volume of air supplied to the lungs in said regulated flow of air;

registration means, connected to said pressure gauge means and to said volume-determining means, for registering said air pressure and said volume over a time period, said air pressure and said volume having a relationship in said time period;

calculator means, supplied from said registration means with said air pressure and said volume registered over said time period, for calculating from said relationship an opening pressure which will inflate at least some alveoli in the lungs; and means for controlling said respiration-assist means to regulate said flow of air dependent on said opening pressure.

2. A ventilator as claimed in claim 1 further comprising:

display means, connected to said calculating means, for displaying said opening pressure.

3. A ventilator as claimed in claim 1 wherein said respiration-assist means includes an expiration line connectable to said patient, an expiratory valve disposed in said expiration line, and control means, connected to said calculation means and to said expiratory valve, for operating said expiratory valve dependent on said opening pressure for maintaining a positive end expiratory pressure, greater than ambient pressure, in the lungs at an end of an expiratory phase of said patient.

4. A ventilator as claimed in claim 3 wherein said control means comprises means for setting a lowest end pressure in the lungs as a selected percent of said opening pressure.

5. A ventilator as claimed in claim 4 wherein said control means comprises means for setting said lowest end pressure in the lungs at a pressure in a range of from 60 to 100% of said opening pressure.

6. A ventilator as claimed in claim 3 wherein said respiration-assist means comprises means for supplying a predetermined volume of air to the lungs during an inspiratory phase of each respiratory cycle of said patient, wherein said registration means comprises means for registering said air pressure in the lungs at the end of said inspiratory phase of each respiratory cycle, wherein said calculating means comprises means for calculating a relative increase in pressure arising in the lungs when said predetermined volume of air is supplied to the lungs and for determining, over a selected number of respiratory cycles, which comprise said time period, whether said relative pressure increase is declining, increasing or is unchanged.

7. A ventilator as claimed in claim 6 wherein said control means comprises means for maintaining said relative increase constant by controlling said respiratory-assist means to vary said positive and expiratory pressure.

8. A ventilator as claimed in claim 1 further comprising means for automatically activating said registration means and said calculator means at specific intervals.

9. A ventilator as claimed in claim 1 wherein said calculating means comprises means for setting said opening pressure at a pressure at which the volume registered by the said registration means exceeds a threshold value.

10. A ventilator as claimed in claim 9 wherein said respiration-assist means includes an expiratory line endotracheally connectable to said patient, an expiratory valve disposed in said expiratory line, and control means for automatically operating said expiratory valve dependent on said opening pressure for maintaining a positive end expiratory pressure, greater than ambient pressure, in the lungs at the end of an expiratory phase of said patient, including setting a lowest end pressure in the lungs as a selected percent of said opening pressure.

11. A ventilator as claimed in claim 9 wherein said respiration-assist means comprises means for supplying a predetermined volume of air to the lungs during said inspiratory phase of each respiratory cycle, wherein said calculation means comprises means for calculating a relative increase in pressure arising in the lungs when said predetermined volume of air is supplied to the lungs and for calculating, over a selected number of respiratory cycles, comprising said time period, whether said relative increase is declining, increasing or is unchanged, and for maintaining said pressure increase constant by controlling said respiration-assist means to vary the positive and expiratory pressure.

12. A ventilator as claimed in claim 1 wherein said calculating means comprises means for setting said opening pressure at a pressure at which a predetermined increase in pressure causes an increase in said volume which exceeds a predetermined volume.

13. A ventilator as claimed in claim 12 wherein said respiration-assist means includes an expiratory line endotracheally connectable to said patient, an expiratory valve disposed in said expiratory line, and control means for automatically operating said expiratory valve dependent on said opening pressure for maintaining a positive end expiratory pressure, greater than ambient pressure, in the lungs at the end of an expiratory phase of said patient, including setting a lowest end pressure in the lungs as a selected percent of said opening pressure.

14. A ventilator as claimed in claim 12 wherein said respiration-assist means comprises means for supplying a predetermined volume of air to the lungs during said inspiratory phase of each respiratory cycle, wherein said calculation means comprises means for calculating a relative increase in pressure arising in the lungs when said predetermined volume of air is supplied to the lungs and for calculating, over a selected number of respiratory cycles, comprising said time period, whether said relative increase is declining, increasing or is unchanged, and for maintaining said pressure increase constant by controlling said respiration-assist means to vary the positive and expiratory pressure.

15. A ventilator as claimed in claim 1 wherein said calculating means comprises means for formulating a curve of air pressure values versus volume values which, within a predetermined interval of said inspiratory phase, is optimally fitted to the air pressure and volume registered by said registration means, and for setting said opening pressure at a pressure at which the fitted curve assumes a predetermined volume value.

16. A ventilator as claimed in claim 15 wherein said calculating means comprises means for setting said opening pressure at a pressure at which said fitted curve assumes a volume value of zero.

17. A ventilator as claimed in claim 15 wherein said calculating means comprises means for fitting said curve to said air pressure and volume registered by said registration means according to the least squares method.

18. A ventilator as claimed in claim 15 wherein said calculating means comprises means for fitting said curve to said air pressure and said volume registered by said registration by fitting a linear curve to said air pressure and said volume registered by said registration means within said predetermined interval of the respiratory phase.

19. A ventilator as claimed in claim 15 wherein said calculating means comprises means for fitting said curve to said air pressure and said volume registered by said registration by fitting a non-linear curve to said air pressure and said volume registered by said registration means within said predetermined interval of the respiratory phase.

20. A ventilator as claimed in claim 15 wherein said calculating means comprises means for formulating said curve within an interval of said respiratory phase between a minimum volume and a maximum volume registered by said registration means.

21. A ventilator as claimed in claim 15 wherein said respiration-assist means includes an expiratory line endotracheally connectable to said patient, an expiratory valve disposed in said expiratory line, and control means for automatically operating said expiratory valve dependent on said opening pressure for maintaining a positive end expiratory pressure, greater than ambient pressure, in the lungs at the end of an expiratory phase of said patient, including setting a lowest end pressure in the lungs as a selected percent of said opening pressure.

22. A ventilator as claimed in claim 15 wherein said respiration-assist means comprises means for supplying a predetermined volume of air to the lungs during said inspiratory phase of each respiratory cycle, wherein said calculation means comprises means for calculating a relative increase in pressure arising in the lungs when said predetermined volume of air is supplied to the lungs and for calculating, over a selected number of respiratory cycles, comprising said time period, whether said relative increase is declining, increasing or is unchanged, and for maintaining said pressure increase constant by controlling said respiration-assist means to vary the positive and expiratory pressure.

* * * * *